United States Patent [19]

Suzuki

[11] 4,309,563

[45] Jan. 5, 1982

[54] XYLYLENE DIOL DERIVATIVE

[75] Inventor: Hiroshi Suzuki, Yokohama, Japan

[73] Assignee: Showa Denko K.K., Tokyo, Japan

[21] Appl. No.: 156,351

[22] Filed: Jun. 4, 1980

[51] Int. Cl.³ .................... C07C 69/76; C07C 69/78; C07C 69/767

[52] U.S. Cl. .................................................. 560/64

[58] Field of Search ....................................... 560/64

[56] References Cited

FOREIGN PATENT DOCUMENTS 53-71033  6/1978  Japan ................................... 560/64

OTHER PUBLICATIONS

Berichte der Deutschen Chemischen Gesellschaft, vol. 70, pp. 1361–1362, (1937).

*Primary Examiner*—Paul J. Killos
*Attorney, Agent, or Firm*—Wenderoth, Lind & Ponack

[57] ABSTRACT

A 3,5-dimethyl-4-alkoxycarbonyl-1,2-xylylene diol of the formula

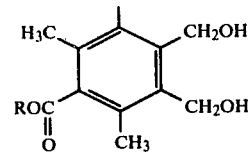

wherein R is an alkyl group having 1 to 4 carbon atoms.

2 Claims, No Drawings

XYLYLENE DIOL DERIVATIVE

This invention provides 3,5-dimethyl-4-alkoxycarbonyl-1,2-xylylene diols of formula (I), novel compounds not described in the literature.

The compounds of this invention can be synthesized by various methods. For example, they can be obtained by a so-called Diels-Alder reaction which comprises reacting an isodehydroacetic acid ester (II) with butynediol (III) under heat, as schematically shown below.

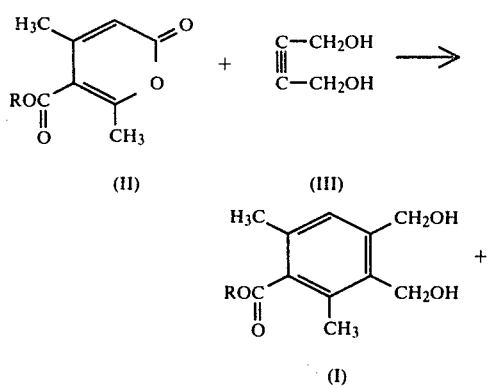

wherein R is an alkyl group having 1 to 4 carbon atoms.

Berichte der Deutschen Chemischen Gesellschaft, Vol. 70, pages 1361–1362 (1937) describes a method for synthesizing a 2,5-dimethyl-4-alkoxycarbonylphthalic acid ester by reacting an isodehydroacetic acid ester (II) with an acetylenedicarboxylic acid ester under heat. It is known however that the yield of the product in this method varies remarkably depending upon the type of the alkyl ester group of the acetylenedicarboxylate (Japanese Laid-Open Patent Publication No. 71033/78). Furthermore, it is generally very rare that such a compound as butynediol is used as a dienophile in the Diels-Alder reaction.

The present inventor has investigated the aforesaid reaction in detail, and found that the compound (I) can be obtained in sufficient practical yields.

In accordance with this invention, the mole ratio of the isodehydroacetate (II) to the butynediol (III) is 1:1.0–5.0, preferably 1:1.5–3.0, and these materials are heated at a reaction temperature in the range of 130° C. to 200° C., preferably 145° to 180° C. for several hours to several days.

EXAMPLE

Butynediol (27.5 parts by weight) was added to 24.5 parts by weight of ethyl isodehydroacetate in a reactor. The air inside the reactor was sufficiently replaced by nitrogen gas, and the reactor was heated at 155° C. over an oil bath to react these materials for about 100 hours. After the reaction, the reaction mixture was passed through a column filled with silica gel using a dichloromethane solvent, and fractions having an ultraviolet adsorption at 254 nanometers were collected. The solvent was distilled off to afford 20.1 g of an orange tar-like crude product.

Recrystallization of the crude product from ether/hexane afforded a purified product having the following analysis data.

Melting point: 54.5° to 56.2° C. (uncorrected).

Elemental analysis (the parenthesized figures are calculated values): C: 65.48% (65.52%), H: 7.68% (7.61%), O: remainder 26.84% (26.87%).

Infrared absorption spectrum (KBr tablet; $cm^{-1}$): 3380, 2980, 2920, 1730, 1610.

Nuclear magnetic resonance spectrum ($CDCl_3$ solvent; trimethylsilane as an internal reference): 7.02 (s), 4.62 (s), 4.58 (s), 4.39 (q), 3.13 (s), 2.30 (s), 2.24 (s), 1.18 (t).

By performing the above procedure using isodehydroacetates of different ester groups, the corresponding compounds having different ester groups at the 4-position were obtained.

The compounds of this invention are useful as intermediates for synthesis of 6,8-dimethyl-7-ethoxycarbonyl-4-hydroxymethyl-1-phthalazone which is a compound having superior antiarteriosclerotic activity.

Reaction of the compound of this invention under alkaline conditions at room temperature or below, preferably 10° C. or below, for several hours using potassium permanganate gives a 3,5-dimethyl-4-alkoxycarbonyl-phthalic acid from which the phthalazone compound can be easily prepared by the method described in U.S. Pat. No. 3,963,716.

What I claim is:

1. A 3,5-dimethyl-4-alkoxycarbonyl-1,2-xylylene diol of the formula

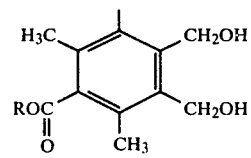

wherein R is an alkyl group having 1 to 4 carbon atoms.

2. 3,5-Dimethyl-4-ethoxycarbonyl-1,2-xylylene diol.

* * * * *